(12) United States Patent
Han (10) Patent No.: US 10,860,684 B2
(45) Date of Patent: Dec. 8, 2020

(54) POLYMERASE PREFERENCE INDEX

(75) Inventor: Jian Han, Huntsville, AL (US)

(73) Assignee: iRepertoire, Inc., Huntsville, AL (US)

( * ) Notice: Subject to any disclaimer, the term of this patent is extended or adjusted under 35 U.S.C. 154(b) by 0 days.

(21) Appl. No.: 13/354,309

(22) Filed: Jan. 19, 2012

(65) Prior Publication Data

US 2012/0303283 A1 Nov. 29, 2012

Related U.S. Application Data

(60) Provisional application No. 61/434,402, filed on Jan. 19, 2011.

(51) Int. Cl.
*G01N 33/48* (2006.01)
*G06F 19/20* (2011.01)
*G06F 19/22* (2011.01)
*G06F 19/28* (2011.01)

(52) U.S. Cl.
CPC .............. *G06F 19/20* (2013.01); *G06F 19/22* (2013.01); *G06F 19/28* (2013.01)

(58) Field of Classification Search
None
See application file for complete search history.

(56) References Cited

U.S. PATENT DOCUMENTS

| | | | | |
|---|---|---|---|---|
| 5,846,719 A | * | 12/1998 | Brenner | B01J 19/0046 435/6.14 |
| 6,143,495 A | * | 11/2000 | Lizardi | C12Q 1/6804 435/6.12 |
| 6,892,141 B1 | | 5/2005 | Nakae et al. | |
| 2003/0068625 A1 | | 4/2003 | Sheehan et al. | |
| 2004/0219565 A1 | * | 11/2004 | Kauppinen | C07H 19/06 435/5 |
| 2006/0047442 A1 | | 3/2006 | Yamamoto | |
| 2006/0057565 A1 | * | 3/2006 | Ju | B82Y 5/00 435/6.12 |
| 2007/0259337 A1 | | 11/2007 | Hully et al. | |
| 2008/0057513 A1 | | 3/2008 | Farrell | |

* cited by examiner

*Primary Examiner* — Anna Skibinsky
(74) *Attorney, Agent, or Firm* — Maynard Cooper & Gale, P. C.; Matthew J. Parker (57) ABSTRACT

Disclosed is a method for calculating a Polymerase Preference Index (PPI) for potential primers for DNA sequencing and/or amplification, and thereby increasing the efficiency of DNA sequencing and/or amplification performed using primers selected according to their PPI number.

3 Claims, 2 Drawing Sheets

Specification includes a Sequence Listing.

| Primers | SEQ ID NO. | A/B | Runway | SEQ ID NO. | C/D |
|---|---|---|---|---|---|
| AAAAAA | SEQ ID NO: 1 | 0.23 | AAAA | SEQ ID NO: 40 | 0.56 |
| AAAAAC | SEQ ID NO: 2 | 0.60 | AAAC | SEQ ID NO: 41 | 0.78 |
| AAAAAG | SEQ ID NO: 3 | 0.37 | AAAG | SEQ ID NO: 42 | 0.76 |
| AAAAAT | SEQ ID NO: 4 | 0.15 | AAAT | SEQ ID NO: 43 | 0.56 |
| AAAACA | SEQ ID NO: 5 | 0.51 | AACA | SEQ ID NO: 44 | 0.87 |
| AAAACC | SEQ ID NO: 6 | 1.30 | AACC | SEQ ID NO: 45 | 0.89 |
| AAAACG | SEQ ID NO: 7 | 1.26 | AACG | SEQ ID NO: 46 | 0.75 |
| AAAACT | SEQ ID NO: 8 | 0.50 | AACT | SEQ ID NO: 47 | 0.77 |
| AAAAGA | SEQ ID NO: 9 | 0.29 | AAGA | SEQ ID NO: 48 | 0.87 |
| AAAAGC | SEQ ID NO: 10 | 0.44 | AAGC | SEQ ID NO: 49 | 0.83 |
| AAAAGG | SEQ ID NO: 11 | 0.66 | AAGG | SEQ ID NO: 50 | 0.77 |
| AAAAGT | SEQ ID NO: 12 | 0.29 | AAGT | SEQ ID NO: 51 | 0.72 |
| AAAATA | SEQ ID NO: 13 | 0.17 | AATA | SEQ ID NO: 52 | 0.83 |
| AAAATC | SEQ ID NO: 14 | 0.41 | AATC | SEQ ID NO: 53 | 0.59 |
| AAAATG | SEQ ID NO: 15 | 0.31 | AATG | SEQ ID NO: 54 | 0.78 |
| AAAATT | SEQ ID NO: 16 | 0.10 | AATT | SEQ ID NO: 55 | 0.70 |
| AAACAA | SEQ ID NO: 17 | 0.61 | ACAA | SEQ ID NO: 56 | 0.82 |
| AAACAC | SEQ ID NO: 18 | 1.48 | ACAC | SEQ ID NO: 57 | 1.08 |
| AAACAG | SEQ ID NO: 19 | 0.41 | ACAG | SEQ ID NO: 58 | 0.90 |
| AAACAT | SEQ ID NO: 20 | 0.59 | ACAT | SEQ ID NO: 59 | 0.89 |
| AAACCA | SEQ ID NO: 21 | 1.60 | ACCA | SEQ ID NO: 60 | 0.67 |
| AAACCC | SEQ ID NO: 22 | 1.89 | ACCC | SEQ ID NO: 61 | 0.86 |
| AAACCG | SEQ ID NO: 23 | 0.96 | ACCG | SEQ ID NO: 62 | 0.73 |
| AAACCT | SEQ ID NO: 24 | 1.87 | ACCT | SEQ ID NO: 63 | 0.83 |
| AAACGA | SEQ ID NO: 25 | 0.76 | ACGA | SEQ ID NO: 64 | 0.73 |
| AAACGC | SEQ ID NO: 26 | 1.19 | ACGC | SEQ ID NO: 65 | 0.80 |
| AAACGG | SEQ ID NO: 27 | 0.91 | ACGG | SEQ ID NO: 66 | 0.97 |
| AAACGT | SEQ ID NO: 28 | 1.83 | ACGT | SEQ ID NO: 67 | 0.80 |
| AAACTA | SEQ ID NO: 29 | 0.49 | ACTA | SEQ ID NO: 68 | 1.03 |
| AAACTC | SEQ ID NO: 30 | 0.74 | ACTC | SEQ ID NO: 69 | 1.36 |
| AAACTG | SEQ ID NO: 31 | 0.65 | ACTG | SEQ ID NO: 70 | 0.68 |
| AAACTT | SEQ ID NO: 32 | 0.32 | ACTT | SEQ ID NO: 71 | 1.34 |
| AAAGAA | SEQ ID NO: 33 | 0.24 | AGAA | SEQ ID NO: 72 | 1.00 |
| AAAGAC | SEQ ID NO: 34 | 0.46 | AGAC | SEQ ID NO: 73 | 1.13 |
| AAAGAG | SEQ ID NO: 35 | 0.38 | AGAG | SEQ ID NO: 74 | 0.89 |
| AAAGAT | SEQ ID NO: 36 | 0.46 | AGAT | SEQ ID NO: 75 | 1.62 |
| AAAGCA | SEQ ID NO: 37 | 0.50 | AGCA | SEQ ID NO: 76 | 1.06 |
| AAAGCC | SEQ ID NO: 38 | 0.74 | AGCC | SEQ ID NO: 77 | 0.61 |
| AAAGCG | SEQ ID NO: 39 | 0.31 | AGCG | SEQ ID NO: 78 | 0.84 |

POLYMERASE PREFERENCE INDEX

This application claims the benefit of priority of U.S. Provisional Application No. 61/434,402, filed Jan. 19, 2011, which is incorporated herein by reference where allowed by applicable law and/or regulation.

FIELD OF THE INVENTION

The invention relates to methods for designing primers which more effectively promote sequencing and/or amplification of DNA and/or RNA sequences.

BACKGROUND OF THE INVENTION

Primers used for sequencing and/or amplification of target DNA and/or RNA sequences must be capable of reliably annealing to a target polynucleotide at a predictable location and must be capable of extension by DNA Polymerase. The success of a Polymerase Chain Reaction (PCR) depends to a significant extent on the correct choice of primers. Selection of primers has traditionally been designed to produce primers that flank, or are contained within, the sequence of interest on a DNA template. Other factors that have been taken into account in primer design include the melting temperature (tm) of each of the primers and of the amplicon, the length of the primers, the length of the amplicon, and the GC content of the sequence. Primers should not form dimers (i.e., the two primers are complementary at both their 3' ends, resulting in very short and competitive products that may interfere with amplification and/or detection of the desired amplification product).

In multiplex PCR, several target sequences are co-amplified, using different primer pairs for each target, so that amplification of all targets is achieved relatively simultaneously. Primer design for these reactions has traditionally taken into account additional factors, such as the need for all amplicons to be competitive, with none being preferentially amplified over the others. Primers should not interfere with one another or form dimers, the formation of dimers being an even more important consideration when multiple sets of primers are introduced.

Primer design methods have been described by others and include, for example, those methods described in U.S. Pat. No. 6,898,531 (Sheehan, et al.); U.S. Pat. No. 6,892,141 (Nakae et al.); U.S. Pat. No. 7,698,069 (Yamamoto); and Lowe, T. et al., "A Computer Program for Selection of Oligonucleotide Primers for PCR," *Nucleic Acids Research* (1990) 18: 1757-1562. However, there is still a need for improvement of the methods of designing and choosing primers and of the primers that are used for DNA amplification, particularly in amplifications where multiple targets must be amplified in one reaction.

SUMMARY OF THE INVENTION

The method of the invention comprises calculating a Polymerase Preference Index (PPI) using Equation I:

$$PPI = A/B * C/D * 100 \quad \text{(Equation I)}$$

(i.e., PPI=A/B×C/D×100) where A is a 6-mer priming frequency, B is a 6-mer frequency observed in resulting amplicons, C is a 4-mer runway frequency, and D is a 4-mer runway frequency observed resulting amplicons, where A/B represents the probability of a 6-mer being used as a primer and C/D represents the probability of a 4-mer being used as a runway sequence. In alternative aspects, the index may also be expressed as PPI=A/B*C/D (Equation II).

The invention also relates to a computer-assisted method for identifying primers for polynucleotide amplification, the method comprising (a) using a computer link to an internet site containing a program for performing the method, entering a target sequence for which one or more primer sequences are desired by a user; (b) performing a search of a DNA sequence database to identify one or more sequences having a desired sequence similarity to that of the target sequence; (c) aligning the one or more sequences to identify one or more conserved regions within the target sequence; (d) applying one or more analysis windows over the target sequence and applying the polymerase preference index to one or more individual 10-nucleotide sequences within the target sequence; (e) identifying one or more potential amplicon regions, with a desirable potential amplicon being defined as a section of DNA of from about 100 to about 250 base pairs, where primer pairs, each primer being approximately 20 base pairs, are identifiable. The method may also include optional steps (f) eliminating potential primer sequences likely to form secondary structures such as hairpin loops and primer dimers; and (g) balancing the results to obtain one or more sets with similar PPIs and to increase or decrease the length of selected primers to identify primers with similar melting temperatures.

BRIEF DESCRIPTION OF THE DRAWINGS

FIG. 2 is a table listing in column 2 the results of analysis of polymerase preference for the 6-nucleotide sequences listed in column 1 and listing in column 4 the results of analysis of polymerase preference for the 4-nucleotide sequences listed in column 3.

DETAILED DESCRIPTION

Figure 1:
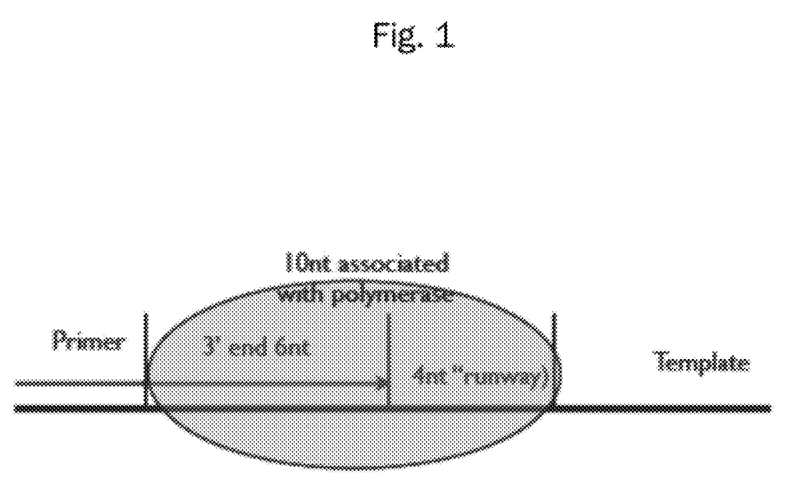
FIG. 1 is an illustration of the position of a DNA polymerase molecule on a single strand of DNA with annealed primer, where "3 end 6 nt" represents a 6-nucleotide sequence at the 3 end of the primer and "4 nt runway" represents a 4-nucleotide sequence of the single-stranded polynucleotide immediately adjacent to the 6-nucleotide sequence that is complementary to the "3 end 6 nt."

The inventor has developed a method for assigning to a proposed primer sequence a Polymerase Preference Index (PPI), with a higher PPI representing a primer that has a higher likelihood of providing a successful amplification result and a lower PPI representing a primer that has a lower likelihood of providing a successful amplification result. As shown in FIG. 1, during DNA synthesis a DNA polymerase is positioned adjacent to a template sequence of approximately 10 nucleotides-6 nucleotides being paired in a double strand with the primer or leading strand, and 4 nucleotides being unpaired until synthesis begins. The inventors refer to this 4-nucleotide sequence as a "runway" sequence because it appears to function much like a section of runway from which an airplane may gather sufficient speed for takeoff. The inventor utilized data from tens of thousands of randomly-generated primer sequences and millions of sequencing reads used to amplify human clinical samples, tabulating the 6-mer priming frequencies and 6-mer frequencies in resulting amplicons, as well as the 4-mer frequencies in resulting amplicons. An example of the results is shown in FIG. 2. From this data, the inventor was able to calculate the PPI using Equation (I):

$$PPI = A/B * C/D * 100 \quad \text{(Equation I)}$$

(i.e., PPI=A/B×C/D×100) where A is the 6-mer priming frequency, obtained from high-throughput sequencing results, B is the 6-mer frequency in resulting amplicons, obtained from high-throughput sequencing (genomic background), C is the 4-mer runway frequency, obtained using high-throughput sequencing results, and D is the 4-mer runway frequency in resulting amplicons (genomic background). In the equation, A/B indicates the probability of a 6-mer being used as a primer and C/D indicates the probability of a 4-mer being used as a runway sequence. A is calculated by determining the number of times a target 6-mer is found at the 5 (5-prime) ends of DNA sequences of amplicons from PCR reactions, and B is calculated by determining the number of times that target 6-mer is found elsewhere in the amplicon sequences. Similarly, C is calculated by determining the number of times that a target 4-mer is found at the 3 (3-prime) end of a target 6-mer in DNA sequences PCR reactions, and D is the number of times that 4-mer sequence is found elsewhere in the amplicon sequences. A sequence may therefore be analyzed to find primers with a greater likelihood of being successfully used by the polymerase (i.e., a greater PPI value) utilizing a 10-nucleotide window for analysis and "sliding" the window (i.e., repositioning the point of analysis) to move to the next 10-nucleotide sequence. The PPI value may be assigned to a particular nucleotide within the sequence, such as, for example, the sixth ($6^{th}$) nucleotide, and additional potential primer sequences may be analyzed by sliding the sequence frame by one nucleotide, for example, to analyze the next possible 10-nucleotide sequence for its polymerase preference index. It is to be understood that primers chosen using the PPI may be used for polynucleotide sequencing and/or amplification.

For an end-user, the method of the invention may be performed using a computer which may link to a website containing links to the input forms and algorithms necessary to perform the analysis. In an alternate method, a program could be loaded onto a user's computer, the program containing the necessary input forms and algorithms, with database information being periodically updated via an internet connection, for example. To perform the method, a user may begin by entering, or copying and pasting, a target sequence into a query box to perform a BLAST search of GenBank sequences. The computer program would then align the most homologous sequences (e.g., the top 50, the top 25, the top 10, etc.) and identify the conserved regions within the target gene. The program would then slide the analysis window over the target sequence and apply the PPI to individual 10-nucleotide sequences within the target sequence. The program then identifies potential amplicon regions, with a desirable amplicon being described as a section of DNA of about 100-250 base pairs, where primer pairs, each primer being approximately 20 base pairs, may be identified. Each of the primers should be located in a conserved region and the 3 end of each primer should be located at a nucleotide that begins a 10-nucleotide sequence with a relatively high PPI. The program will then eliminate potential primer sequences likely to form secondary structures such as hairpin loops and primer dimers. The panel of potential primers is then balanced to obtain sets with similar PPIs and to increase or decrease the length of the primers to select primers with similar TMs.

In certain aspects of the method, a primer that is selected may be assigned a unique identification tag which may be associated with background information about the characteristics of the primer.

The inventor has previously described a method for performing multiplex amplification of target samples (arm-PCR), which has been disclosed in an application published under the Patent Cooperation Treaty (WO2009/124293) and in U.S. Patent Application Publication Number US20090253183A1. Primers designed using the method of the present invention may be utilized in the arm-PCR technique as follows: the 30-mer tag may be linked to the gene-specific primer and introduced into PCR products during arm-PCR amplification. The same sequence may be used as a capture probe, printed onto a universal array. PCR products may then hybridize to the specific capture probe and be recognized based upon the signal resulting from hybridization. The 30-mer tag may be inserted into either $R_i$ or $F_i$ primers (described in WO2009/124293, for the arm-PCR method), between the common (communal) primer tag and the gene-specific primer. Generally, the communal primer will be positioned with the $F_i$ primer and will be labeled. The 30-mer tag will generally be inserted into the $R_i$ primer, making sure that the 30-mer tag will not form a hairpin loop with the primer.

The invention may be further described by means of the following non-limiting examples.

EXAMPLES

Example 1

Calculation of PPI Values

Human genomic DNA was segmented using the computer so that sequences of 300 base pairs could be analyzed. Two hundred randomly-selected fragments of sequence of genomic DNA were used to design random primers. Those same 200 sequences were used in conjunction with software available online to design primers, with selection based primarily on the TM (melting temperature). The random primers were selected by starting from base 50-70 (forward) and 200-180 (reverse). Comparing the two groups, the inventor discovered that the random primers gave a rate of successful amplification of about 50 percent, while the primers selected based upon TM fared better (about 80 percent). However, the failure rate was still about 20 percent.

The rapidity of obtaining results using high-throughput sequencing then allowed the inventor to utilize 454 sequencing to perform 8 runs and compile the frequencies from over 4.4 million reads. These results, when analyzed using the algorithm represented by Equation I, demonstrated that there is a preferential relationship between DNA polymerase and certain sequences. A small sampling of the inventor' results is shown in FIG. 2. Using these results, the inventor has designed primers that significantly increase the amplification efficiency for selected sequences over that obtained using random or melting temperature analysis.

What is claimed is:

1. A method for producing primers to improve the efficiency of amplification by a polymerase, the method comprising:
   a) performing multiple amplifications using randomly-generated primers to amplify target sequences using a polymerase, each randomly-generated primer comprising a sequence of about 20 nucleotides, the 3' end of each primer binding to a 6-mer of a 10-nucleotide sequence in a target sequence, wherein the remaining 4-mer of the 10-nucleotide sequence comprises a runway sequence, thereby producing amplicons;

b) selecting at least one primer with the greatest polymerase preference index, the polymerase preference index determined by the multiple of a first percentage, representing the number of times a 6-mer of the 10-nucleotide sequence is found at the 5-prime ends of amplicons from the multiple amplifications divided by the number of times the 6-mer is found elsewhere in the amplicons, and a second percentage representing the number of times that a 4-mer of the 10-nucleotide sequence is found at the 3-prime end of a the 6-mer in the amplicons divided by the number of times that the 4-mer is found elsewhere in the amplicon sequences; and c) performing amplification of at least one target sequence using at least one primer selected with the greatest polymerase preference index.

2. The method of claim 1, wherein at least two primers with the greatest polymerase preference index are selected.

3. The method of claim 2, wherein the lengths of the at least two primers with the greatest polymerase preference index are increased or decreased to produce primers with approximately the same melting temperatures.

* * * * *

SEQUENCE LISTING

<160> NUMBER OF SEQ ID NOS: 78

<210> SEQ ID NO 1
<211> LENGTH: 6
<212> TYPE: DNA
<213> ORGANISM: Artificial Sequence
<220> FEATURE:
<223> OTHER INFORMATION: Primer sequence
<220> FEATURE:
<221> NAME/KEY: prim_transcript
<222> LOCATION: (1)..(6)

<400> SEQUENCE: 1 aaaaaa                                                                    6

<210> SEQ ID NO 2
<211> LENGTH: 6
<212> TYPE: DNA
<213> ORGANISM: Artificial Sequence
<220> FEATURE:
<223> OTHER INFORMATION: Primer Sequence

<400> SEQUENCE: 2 aaaaac                                                                    6

<210> SEQ ID NO 3
<211> LENGTH: 6
<212> TYPE: DNA
<213> ORGANISM: Artificial Sequence
<220> FEATURE:
<223> OTHER INFORMATION: Primer sequence

<400> SEQUENCE: 3 aaaaag                                                                    6

<210> SEQ ID NO 4
<211> LENGTH: 6
<212> TYPE: DNA
<213> ORGANISM: Artificial Sequence
<220> FEATURE:
<223> OTHER INFORMATION: Primer sequence

<400> SEQUENCE: 4 aaaaat                                                                    6

<210> SEQ ID NO 5
<211> LENGTH: 6
<212> TYPE: DNA
<213> ORGANISM: Artificial Sequence
<220> FEATURE:
<223> OTHER INFORMATION: Primer sequence

<400> SEQUENCE: 5 aaaaca                                                                    6

<210> SEQ ID NO 6
<211> LENGTH: 6
<212> TYPE: DNA
<213> ORGANISM: Artificial Sequence
<220> FEATURE:
<223> OTHER INFORMATION: Primer sequence

<400> SEQUENCE: 6 aaaacc                                                                    6

<210> SEQ ID NO 7

```
<211> LENGTH: 6
<212> TYPE: DNA
<213> ORGANISM: Artificial Sequence
<220> FEATURE:
<223> OTHER INFORMATION: Primer sequence

<400> SEQUENCE: 7 aaaacg                                                                    6

<210> SEQ ID NO 8
<211> LENGTH: 6
<212> TYPE: DNA
<213> ORGANISM: Artificial Sequence
<220> FEATURE:
<223> OTHER INFORMATION: Primer sequence

<400> SEQUENCE: 8 aaaact                                                                    6

<210> SEQ ID NO 9
<211> LENGTH: 6
<212> TYPE: DNA
<213> ORGANISM: Artificial Sequence
<220> FEATURE:
<223> OTHER INFORMATION: Primer sequence

<400> SEQUENCE: 9 aaaaga                                                                    6

<210> SEQ ID NO 10
<211> LENGTH: 6
<212> TYPE: DNA
<213> ORGANISM: Artificial Sequence
<220> FEATURE:
<223> OTHER INFORMATION: Primer sequence

<400> SEQUENCE: 10 aaaagc                                                                    6

<210> SEQ ID NO 11
<211> LENGTH: 6
<212> TYPE: DNA
<213> ORGANISM: Artificial Sequence
<220> FEATURE:
<223> OTHER INFORMATION: Primer sequence

<400> SEQUENCE: 11 aaaagg                                                                    6

<210> SEQ ID NO 12
<211> LENGTH: 6
<212> TYPE: DNA
<213> ORGANISM: Artificial Sequence
<220> FEATURE:
<223> OTHER INFORMATION: Primer sequence

<400> SEQUENCE: 12 aaaagt                                                                    6

<210> SEQ ID NO 13
<211> LENGTH: 6
<212> TYPE: DNA
<213> ORGANISM: Artificial Sequence
<220> FEATURE:
<223> OTHER INFORMATION: Primer sequence

<400> SEQUENCE: 13
``` aaaata                                                          6

<210> SEQ ID NO 14
<211> LENGTH: 6
<212> TYPE: DNA
<213> ORGANISM: Artificial Sequence
<220> FEATURE:
<223> OTHER INFORMATION: Primer sequence

<400> SEQUENCE: 14 aaaatc                                                          6

<210> SEQ ID NO 15
<211> LENGTH: 6
<212> TYPE: DNA
<213> ORGANISM: Artificial Sequence
<220> FEATURE:
<223> OTHER INFORMATION: Primer sequence

<400> SEQUENCE: 15 aaaatg                                                          6

<210> SEQ ID NO 16
<211> LENGTH: 6
<212> TYPE: DNA
<213> ORGANISM: Artificial Sequence
<220> FEATURE:
<223> OTHER INFORMATION: Primer sequence

<400> SEQUENCE: 16 aaaatt                                                          6

<210> SEQ ID NO 17
<211> LENGTH: 6
<212> TYPE: DNA
<213> ORGANISM: Artificial Sequence
<220> FEATURE:
<223> OTHER INFORMATION: Primer sequence

<400> SEQUENCE: 17 aaacaa                                                          6

<210> SEQ ID NO 18
<211> LENGTH: 6
<212> TYPE: DNA
<213> ORGANISM: Artificial Sequence
<220> FEATURE:
<223> OTHER INFORMATION: Primer sequence

<400> SEQUENCE: 18 aaacac                                                          6

<210> SEQ ID NO 19
<211> LENGTH: 6
<212> TYPE: DNA
<213> ORGANISM: Artificial Sequence
<220> FEATURE:
<223> OTHER INFORMATION: Primer sequence

<400> SEQUENCE: 19 aaacag                                                          6

<210> SEQ ID NO 20
<211> LENGTH: 6
<212> TYPE: DNA

```
<213> ORGANISM: Artificial Sequence
<220> FEATURE:
<223> OTHER INFORMATION: Primer sequence

<400> SEQUENCE: 20 aaacat                                                                    6

<210> SEQ ID NO 21
<211> LENGTH: 6
<212> TYPE: DNA
<213> ORGANISM: Artificial Sequence
<220> FEATURE:
<223> OTHER INFORMATION: Primer sequence

<400> SEQUENCE: 21 aaacca                                                                    6

<210> SEQ ID NO 22
<211> LENGTH: 6
<212> TYPE: DNA
<213> ORGANISM: Artificial Sequence
<220> FEATURE:
<223> OTHER INFORMATION: Primer sequence

<400> SEQUENCE: 22 aaaccc                                                                    6

<210> SEQ ID NO 23
<211> LENGTH: 6
<212> TYPE: DNA
<213> ORGANISM: Artificial Sequence
<220> FEATURE:
<223> OTHER INFORMATION: Primer sequence

<400> SEQUENCE: 23 aaaccg                                                                    6

<210> SEQ ID NO 24
<211> LENGTH: 6
<212> TYPE: DNA
<213> ORGANISM: Artificial Sequence
<220> FEATURE:
<223> OTHER INFORMATION: Primer sequence

<400> SEQUENCE: 24 aaacct                                                                    6

<210> SEQ ID NO 25
<211> LENGTH: 6
<212> TYPE: DNA
<213> ORGANISM: Artificial Sequence
<220> FEATURE:
<223> OTHER INFORMATION: Primer sequence

<400> SEQUENCE: 25 aaacga                                                                    6

<210> SEQ ID NO 26
<211> LENGTH: 6
<212> TYPE: DNA
<213> ORGANISM: Artificial Sequence
<220> FEATURE:
<223> OTHER INFORMATION: Primer sequence

<400> SEQUENCE: 26 aaacgc                                                                    6
```

```
<210> SEQ ID NO 27
<211> LENGTH: 6
<212> TYPE: DNA
<213> ORGANISM: Artificial Sequence
<220> FEATURE:
<223> OTHER INFORMATION: Primer sequence

<400> SEQUENCE: 27 aaacgg                                                                    6

<210> SEQ ID NO 28
<211> LENGTH: 6
<212> TYPE: DNA
<213> ORGANISM: Artificial Sequence
<220> FEATURE:
<223> OTHER INFORMATION: Primer sequence

<400> SEQUENCE: 28 aaacgt                                                                    6

<210> SEQ ID NO 29
<211> LENGTH: 6
<212> TYPE: DNA
<213> ORGANISM: Artificial Sequence
<220> FEATURE:
<223> OTHER INFORMATION: Primer sequence

<400> SEQUENCE: 29 aaacta                                                                    6

<210> SEQ ID NO 30
<211> LENGTH: 6
<212> TYPE: DNA
<213> ORGANISM: Artificial Sequence
<220> FEATURE:
<223> OTHER INFORMATION: Primer sequence

<400> SEQUENCE: 30 aaactc                                                                    6

<210> SEQ ID NO 31
<211> LENGTH: 6
<212> TYPE: DNA
<213> ORGANISM: Artificial Sequence
<220> FEATURE:
<223> OTHER INFORMATION: Primer sequence

<400> SEQUENCE: 31 aaactg                                                                    6

<210> SEQ ID NO 32
<211> LENGTH: 6
<212> TYPE: DNA
<213> ORGANISM: Artificial Sequence
<220> FEATURE:
<223> OTHER INFORMATION: Primer sequence

<400> SEQUENCE: 32 aaactt                                                                    6

<210> SEQ ID NO 33
<211> LENGTH: 6
<212> TYPE: DNA
<213> ORGANISM: Artificial Sequence
<220> FEATURE:
```

```
<223> OTHER INFORMATION: Primer sequence

<400> SEQUENCE: 33 aaagaa                                                                    6

<210> SEQ ID NO 34
<211> LENGTH: 6
<212> TYPE: DNA
<213> ORGANISM: Artificial Sequence
<220> FEATURE:
<223> OTHER INFORMATION: Primer sequence

<400> SEQUENCE: 34 aaagac                                                                    6

<210> SEQ ID NO 35
<211> LENGTH: 6
<212> TYPE: DNA
<213> ORGANISM: Artificial Sequence
<220> FEATURE:
<223> OTHER INFORMATION: Primer sequence

<400> SEQUENCE: 35 aaagag                                                                    6

<210> SEQ ID NO 36
<211> LENGTH: 6
<212> TYPE: DNA
<213> ORGANISM: Artificial Sequence
<220> FEATURE:
<223> OTHER INFORMATION: Primer sequence

<400> SEQUENCE: 36 aaagat                                                                    6

<210> SEQ ID NO 37
<211> LENGTH: 6
<212> TYPE: DNA
<213> ORGANISM: Artificial Sequence
<220> FEATURE:
<223> OTHER INFORMATION: Primer sequence

<400> SEQUENCE: 37 aaagca                                                                    6

<210> SEQ ID NO 38
<211> LENGTH: 6
<212> TYPE: DNA
<213> ORGANISM: Artificial Sequence
<220> FEATURE:
<223> OTHER INFORMATION: Primer sequence

<400> SEQUENCE: 38 aaagcc                                                                    6

<210> SEQ ID NO 39
<211> LENGTH: 6
<212> TYPE: DNA
<213> ORGANISM: Artificial Sequence
<220> FEATURE:
<223> OTHER INFORMATION: Primer sequence

<400> SEQUENCE: 39 aaagcg                                                                    6
```

```
<210> SEQ ID NO 40
<211> LENGTH: 4
<212> TYPE: DNA
<213> ORGANISM: Artificial Sequence
<220> FEATURE:
<223> OTHER INFORMATION: Primer sequence

<400> SEQUENCE: 40 aaaa                                                                4

<210> SEQ ID NO 41
<211> LENGTH: 4
<212> TYPE: DNA
<213> ORGANISM: Artificial Sequence
<220> FEATURE:
<223> OTHER INFORMATION: Primer sequence

<400> SEQUENCE: 41 aaac                                                                4

<210> SEQ ID NO 42
<211> LENGTH: 4
<212> TYPE: DNA
<213> ORGANISM: Artificial Sequence
<220> FEATURE:
<223> OTHER INFORMATION: Primer sequence

<400> SEQUENCE: 42 aaag                                                                4

<210> SEQ ID NO 43
<211> LENGTH: 4
<212> TYPE: DNA
<213> ORGANISM: Artificial Sequence
<220> FEATURE:
<223> OTHER INFORMATION: Primer sequence

<400> SEQUENCE: 43 aaat                                                                4

<210> SEQ ID NO 44
<211> LENGTH: 4
<212> TYPE: DNA
<213> ORGANISM: Artificial Sequence
<220> FEATURE:
<223> OTHER INFORMATION: Primer sequence

<400> SEQUENCE: 44 aaca                                                                4

<210> SEQ ID NO 45
<211> LENGTH: 4
<212> TYPE: DNA
<213> ORGANISM: Artificial Sequence
<220> FEATURE:
<223> OTHER INFORMATION: Primer sequence

<400> SEQUENCE: 45 aacc                                                                4

<210> SEQ ID NO 46
<211> LENGTH: 4
<212> TYPE: DNA
<213> ORGANISM: Artificial Sequence
<220> FEATURE:
<223> OTHER INFORMATION: Primer sequence
```

```
<400> SEQUENCE: 46 aacg                                                                    4

<210> SEQ ID NO 47
<211> LENGTH: 4
<212> TYPE: DNA
<213> ORGANISM: Artificial Sequence
<220> FEATURE:
<223> OTHER INFORMATION: Primer sequence

<400> SEQUENCE: 47 aact                                                                    4

<210> SEQ ID NO 48
<211> LENGTH: 4
<212> TYPE: DNA
<213> ORGANISM: Artificial Sequence
<220> FEATURE:
<223> OTHER INFORMATION: Primer sequence

<400> SEQUENCE: 48 aaga                                                                    4

<210> SEQ ID NO 49
<211> LENGTH: 4
<212> TYPE: DNA
<213> ORGANISM: Artificial Sequence
<220> FEATURE:
<223> OTHER INFORMATION: Primer sequence

<400> SEQUENCE: 49 aagc                                                                    4

<210> SEQ ID NO 50
<211> LENGTH: 4
<212> TYPE: DNA
<213> ORGANISM: Artificial Sequence
<220> FEATURE:
<223> OTHER INFORMATION: Primer sequence

<400> SEQUENCE: 50 aagg                                                                    4

<210> SEQ ID NO 51
<211> LENGTH: 4
<212> TYPE: DNA
<213> ORGANISM: Artificial Sequence
<220> FEATURE:
<223> OTHER INFORMATION: Primer sequence

<400> SEQUENCE: 51 aagt                                                                    4

<210> SEQ ID NO 52
<211> LENGTH: 4
<212> TYPE: DNA
<213> ORGANISM: Artificial Sequence
<220> FEATURE:
<223> OTHER INFORMATION: Primer sequence

<400> SEQUENCE: 52 aata                                                                    4

<210> SEQ ID NO 53
<211> LENGTH: 4
```

```
<212> TYPE: DNA
<213> ORGANISM: Artificial Sequence
<220> FEATURE:
<223> OTHER INFORMATION: Primer sequence

<400> SEQUENCE: 53 aatc                                                                    4

<210> SEQ ID NO 54
<211> LENGTH: 4
<212> TYPE: DNA
<213> ORGANISM: Artificial Sequence
<220> FEATURE:
<223> OTHER INFORMATION: Primer sequence

<400> SEQUENCE: 54 aatg                                                                    4

<210> SEQ ID NO 55
<211> LENGTH: 4
<212> TYPE: DNA
<213> ORGANISM: Artificial Sequence
<220> FEATURE:
<223> OTHER INFORMATION: Primer sequence

<400> SEQUENCE: 55 aatt                                                                    4

<210> SEQ ID NO 56
<211> LENGTH: 4
<212> TYPE: DNA
<213> ORGANISM: Artificial Sequence
<220> FEATURE:
<223> OTHER INFORMATION: Primer sequence

<400> SEQUENCE: 56 acaa                                                                    4

<210> SEQ ID NO 57
<211> LENGTH: 4
<212> TYPE: DNA
<213> ORGANISM: Artificial Sequence
<220> FEATURE:
<223> OTHER INFORMATION: Primer sequence

<400> SEQUENCE: 57 acac                                                                    4

<210> SEQ ID NO 58
<211> LENGTH: 4
<212> TYPE: DNA
<213> ORGANISM: Artificial Sequence
<220> FEATURE:
<223> OTHER INFORMATION: Primer sequence

<400> SEQUENCE: 58 acag                                                                    4

<210> SEQ ID NO 59
<211> LENGTH: 4
<212> TYPE: DNA
<213> ORGANISM: Artificial Sequence
<220> FEATURE:
<223> OTHER INFORMATION: Primer sequence

<400> SEQUENCE: 59
``` acat                                                                        4

<210> SEQ ID NO 60
<211> LENGTH: 4
<212> TYPE: DNA
<213> ORGANISM: Artificial Sequence
<220> FEATURE:
<223> OTHER INFORMATION: Primer sequence

<400> SEQUENCE: 60 acca                                                                        4

<210> SEQ ID NO 61
<211> LENGTH: 4
<212> TYPE: DNA
<213> ORGANISM: Artificial Sequence
<220> FEATURE:
<223> OTHER INFORMATION: Primer sequence

<400> SEQUENCE: 61 accc                                                                        4

<210> SEQ ID NO 62
<211> LENGTH: 4
<212> TYPE: DNA
<213> ORGANISM: Artificial Sequence
<220> FEATURE:
<223> OTHER INFORMATION: Primer sequence

<400> SEQUENCE: 62 accg                                                                        4

<210> SEQ ID NO 63
<211> LENGTH: 4
<212> TYPE: DNA
<213> ORGANISM: Artificial Sequence
<220> FEATURE:
<223> OTHER INFORMATION: Primer sequence

<400> SEQUENCE: 63 acct                                                                        4

<210> SEQ ID NO 64
<211> LENGTH: 4
<212> TYPE: DNA
<213> ORGANISM: Artificial Sequence
<220> FEATURE:
<223> OTHER INFORMATION: Primer sequence

<400> SEQUENCE: 64 acga                                                                        4

<210> SEQ ID NO 65
<211> LENGTH: 4
<212> TYPE: DNA
<213> ORGANISM: Artificial Sequence
<220> FEATURE:
<223> OTHER INFORMATION: Primer sequence

<400> SEQUENCE: 65 acgc                                                                        4

<210> SEQ ID NO 66
<211> LENGTH: 4
<212> TYPE: DNA
<213> ORGANISM: Artificial Sequence

```
<220> FEATURE:
<223> OTHER INFORMATION: Primer sequence

<400> SEQUENCE: 66 acgg                                                                4

<210> SEQ ID NO 67
<211> LENGTH: 4
<212> TYPE: DNA
<213> ORGANISM: Artificial Sequence
<220> FEATURE:
<223> OTHER INFORMATION: Primer sequence

<400> SEQUENCE: 67 acgt                                                                4

<210> SEQ ID NO 68
<211> LENGTH: 4
<212> TYPE: DNA
<213> ORGANISM: Artificial Sequence
<220> FEATURE:
<223> OTHER INFORMATION: Primer sequence

<400> SEQUENCE: 68 acta                                                                4

<210> SEQ ID NO 69
<211> LENGTH: 4
<212> TYPE: DNA
<213> ORGANISM: Artificial Sequence
<220> FEATURE:
<223> OTHER INFORMATION: Primer sequence

<400> SEQUENCE: 69 actc                                                                4

<210> SEQ ID NO 70
<211> LENGTH: 4
<212> TYPE: DNA
<213> ORGANISM: Artificial Sequence
<220> FEATURE:
<223> OTHER INFORMATION: Primer sequence

<400> SEQUENCE: 70 actg                                                                4

<210> SEQ ID NO 71
<211> LENGTH: 4
<212> TYPE: DNA
<213> ORGANISM: Artificial Sequence
<220> FEATURE:
<223> OTHER INFORMATION: Primer sequence

<400> SEQUENCE: 71 actt                                                                4

<210> SEQ ID NO 72
<211> LENGTH: 4
<212> TYPE: DNA
<213> ORGANISM: Artificial Sequence
<220> FEATURE:
<223> OTHER INFORMATION: Primer sequence

<400> SEQUENCE: 72 agaa                                                                4
```

```
<210> SEQ ID NO 73
<211> LENGTH: 4
<212> TYPE: DNA
<213> ORGANISM: Artificial Sequence
<220> FEATURE:
<223> OTHER INFORMATION: Primer sequence

<400> SEQUENCE: 73 agac                                                                    4

<210> SEQ ID NO 74
<211> LENGTH: 4
<212> TYPE: DNA
<213> ORGANISM: Artificial Sequence
<220> FEATURE:
<223> OTHER INFORMATION: Primer sequence

<400> SEQUENCE: 74 agag                                                                    4

<210> SEQ ID NO 75
<211> LENGTH: 4
<212> TYPE: DNA
<213> ORGANISM: Artificial Sequence
<220> FEATURE:
<223> OTHER INFORMATION: Primer sequence

<400> SEQUENCE: 75 agat                                                                    4

<210> SEQ ID NO 76
<211> LENGTH: 4
<212> TYPE: DNA
<213> ORGANISM: Artificial Sequence
<220> FEATURE:
<223> OTHER INFORMATION: Primer sequence

<400> SEQUENCE: 76 agca                                                                    4

<210> SEQ ID NO 77
<211> LENGTH: 4
<212> TYPE: DNA
<213> ORGANISM: Artificial Sequence
<220> FEATURE:
<223> OTHER INFORMATION: Primer sequence

<400> SEQUENCE: 77 agcc                                                                    4

<210> SEQ ID NO 78
<211> LENGTH: 4
<212> TYPE: DNA
<213> ORGANISM: Artificial Sequence
<220> FEATURE:
<223> OTHER INFORMATION: Primer sequence

<400> SEQUENCE: 78 agcg                                                                    4
```